United States Patent [19]

Roshdy

[11] Patent Number: 5,427,243

[45] Date of Patent: Jun. 27, 1995

[54] TEMPORARY PACING WIRE PACKAGE

[75] Inventor: Constance Roshdy, New Egypt, N.J.

[73] Assignee: Ethicon, Inc., Somerville, N.J.

[21] Appl. No.: 259,834

[22] Filed: Jun. 15, 1994

[51] Int. Cl.⁶ ............................................. B65D 85/38
[52] U.S. Cl. ................................. 206/438; 206/63.3; 206/380
[58] Field of Search ................. 206/63.3, 227, 380, 206/388, 438

[56] References Cited

U.S. PATENT DOCUMENTS

| 4,120,395 | 10/1978 | Mandel et al. | 206/63.3 |
| 5,169,002 | 12/1992 | Evans et al. | 206/438 |
| 5,174,087 | 12/1992 | Bruno | 206/63.3 |
| 5,199,561 | 4/1993 | Roshdy et al. | 206/63.3 |
| 5,277,299 | 1/1994 | Holzwarth et al. | 206/380 |
| 5,348,146 | 9/1994 | Sterling et al. | 206/63.3 |
| 5,358,624 | 10/1994 | Roshdy et al. | 206/63.3 |

Primary Examiner—Jimmy G. Foster
Attorney, Agent, or Firm—Emil Richard Skula

[57] ABSTRACT

A foldable package for a temporary cardiac pacing wire is disclosed. The package has a plurality of panels connected along fold lines as well as holes and tab pockets for mounting surgical needles and electrode needles. The package also has tabs and tab pockets for locking the package.

5 Claims, 4 Drawing Sheets

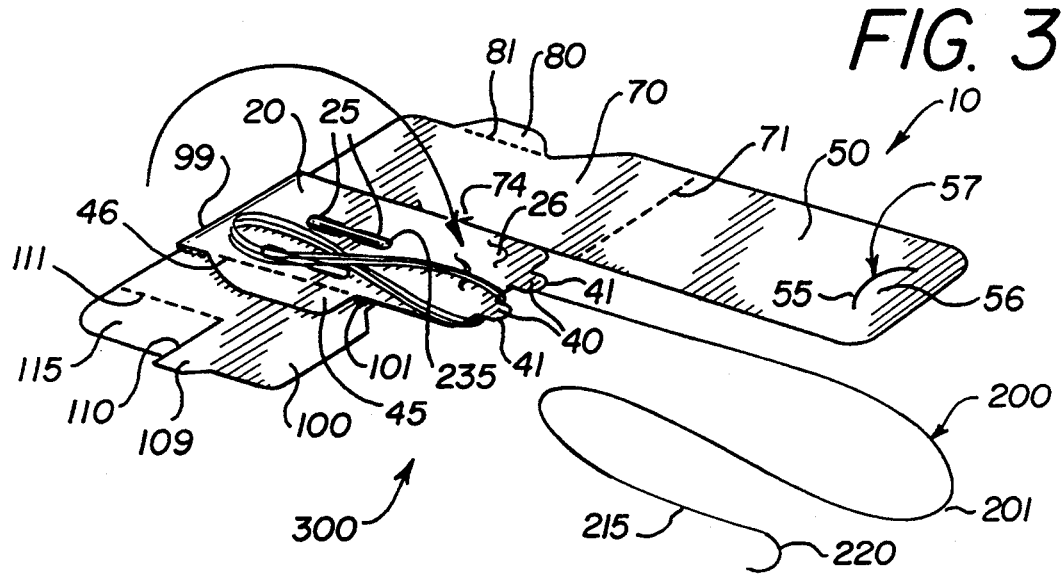
FIG. 3
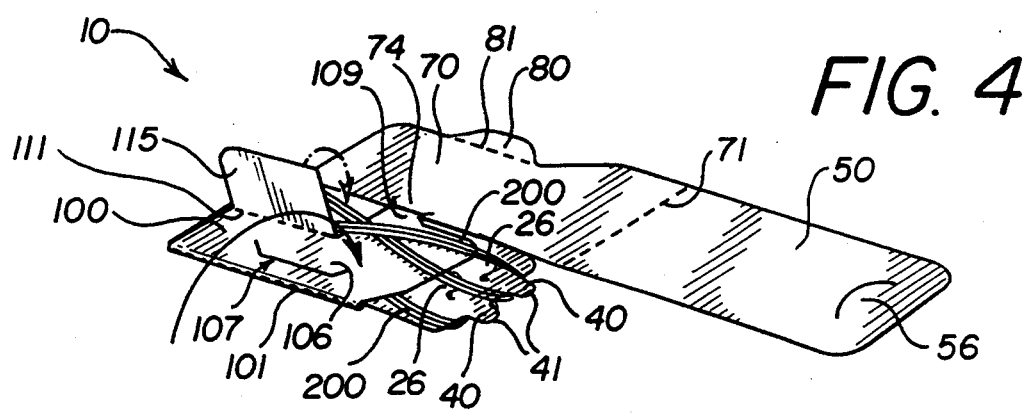
FIG. 4
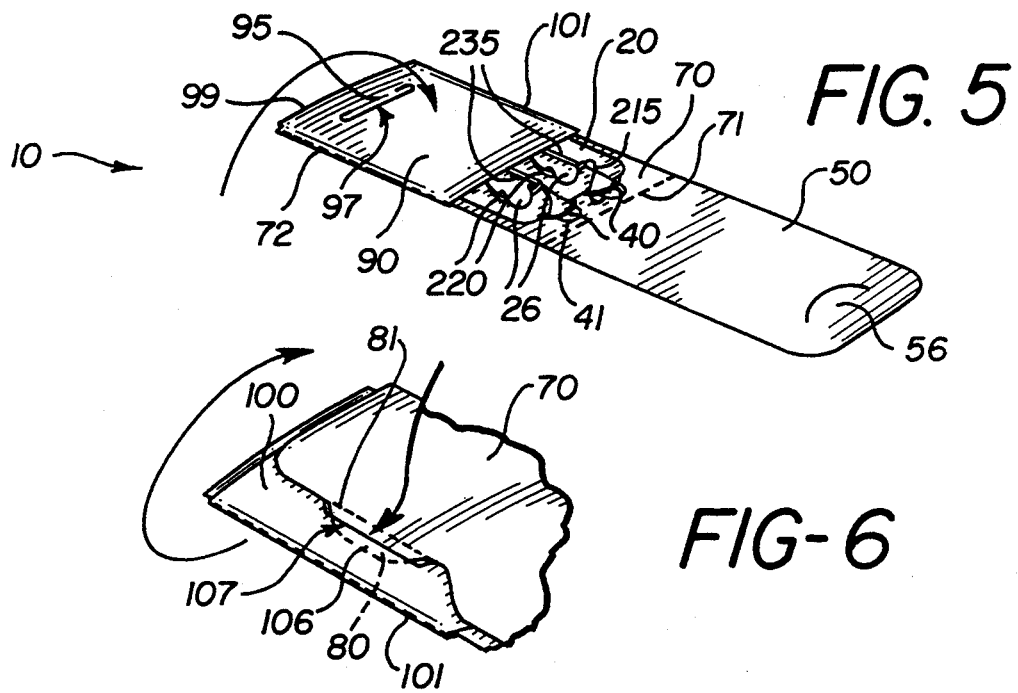
FIG. 5
FIG-6

TEMPORARY PACING WIRE PACKAGE

TECHNICAL FIELD

The field of art to which this invention relates is packaging, in particular, packaging for medical devices.

BACKGROUND OF THE INVENTION

Temporary cardiac pacing wires have long been used to stabilize heart patients, particularly after major cardiac surgery. The pacing wires typically consist of an insulated lead having a distal section of bare conductor to which a surgical needle is attached. A straight electrode needle, typically having a score line, is mounted to the proximal end of the insulated conductor. The pacing wires are typically used by inserting the surgical needle into and through the cardiac muscle of a patient's heart such that the bare conductive section is within the cardiac muscle. The bare conductor is then typically tied and stitched in place in the cardiac muscle, and the surgical needle is typically cut off from the bare conductive section. Next, the electrode needles are typically pushed through the chest wall (from interior to exterior) and a sufficient section of the insulated conductor is pulled through so that the electrode needle can effectively be inserted into a monitoring/pacing device. Typically, the pointed end of the electrode needle is broken from the needle body along the score line prior to insertion. The resulting electrode section is plugged directly into a receptacle in the monitoring/pacing device.

There is a constant need in this art for improved packages for pacing needles which protect the needles and conductors during sterilization, shipping and packaging but are easy to work with in the operating room. In particular, the pacing leads and needles should be readily accessible and easily removed from the package when needed by the surgeon during a cardiac surgical procedure.

SUMMARY OF THE INVENTION

It is an object of the present invention to provide a foldable package for one or more cardiac pacing leads wherein the package protects the pacing leads during sterilization, shipping and handling, and from which the pacing leads may be easily accessed and removed in the operating room.

Accordingly, a foldable package for a cardiac pacing lead is disclosed. The package has a base panel having a pair of substantially opposed major sides and a pair of substantially opposed minor sides. At least one winding tab extends from a first minor side of the base panel. The base panel has means for receiving a surgical needle and means for receiving an electrode needle. A tab panel is foldably connected to one major side of the base panel. A front retention panel is foldably connected to the second minor side of the base panel. The front retention panel has a pair of substantially opposed major sides and a pair of substantially opposed minor sides. A tab pocket in the front retention panel receives a tab. A back cover panel having a pair of substantially opposed major sides and substantially opposed sides is foldably connected along a first major side to the first major side of the front retention panel. A tab is foldably connected to the second major side of the back cover panel. A tab pocket in the back cover panel receives a tab. A front cover panel having a pair of substantially opposed major sides and a pair of substantially opposed minor sides is foldably connected to a first minor side of the back cover panel. A tab pocket is located in the front cover panel. A back retention panel having a pair of opposed major sides and a pair of opposed minor sides is foldably connected along its first major side to the second major side of the front retention panel. A tab member extends from the second major side of the back retention panel. A tab pocket is located in the back retention panel. A fold line and a slit are contained in the back retention panel forming a tab member. The tab pocket of the back retention panel receives the tab member of the back cover panel.

An additional aspect of the present invention is the combination of the above-described package and at least one temporary cardiac pacing lead.

BRIEF DESCRIPTION OF THE DRAWINGS

FIGS. 3-7 are perspective views of the assembly steps typically used to package a cardiac pacing lead in the package of the present invention.

DESCRIPTION OF PREFERRED EMBODIMENTS

Figure 1:
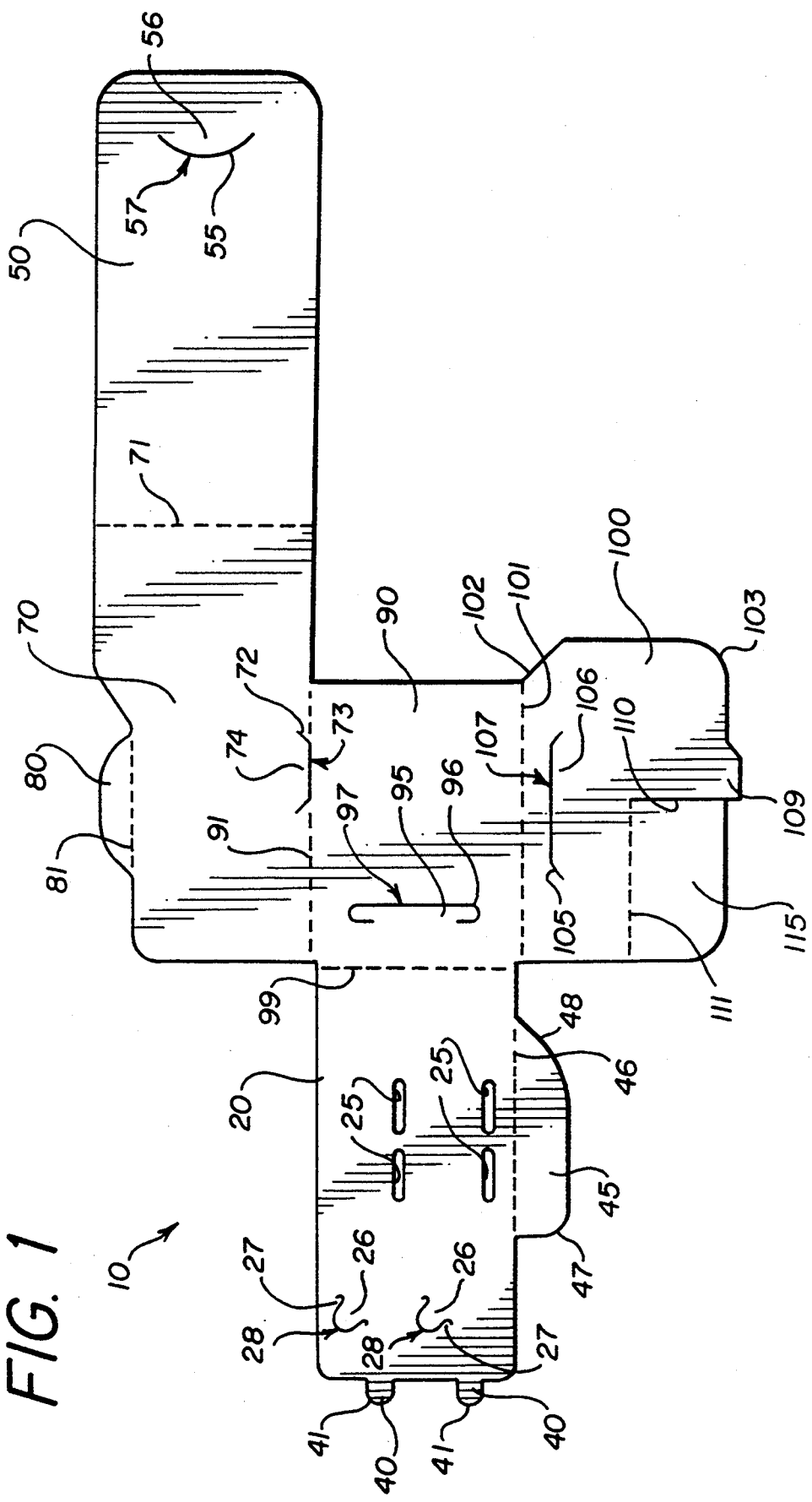
FIG. 1 is a plan view of the cardiac pacing lead package of the present invention.
Figure 2:
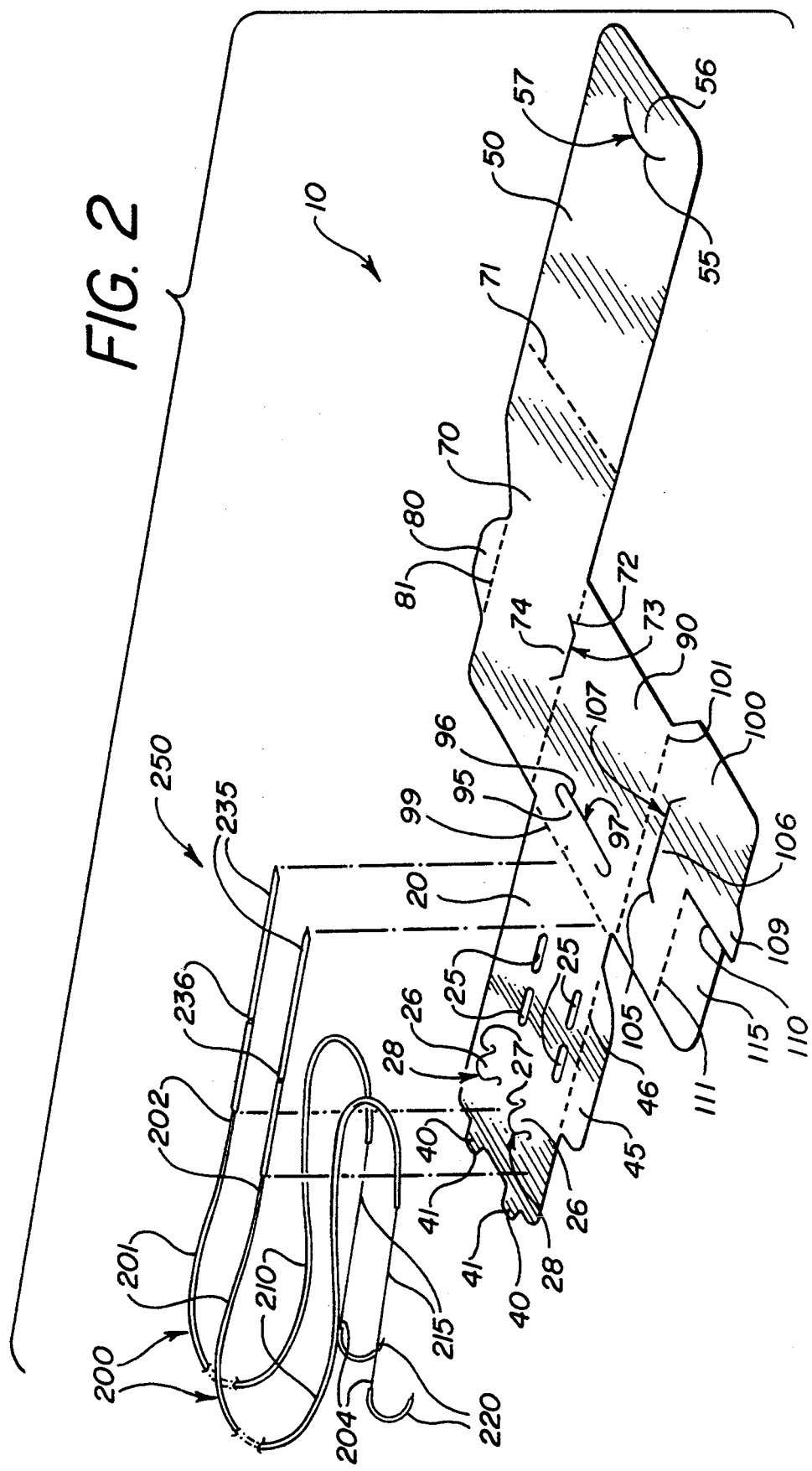
FIG. 2 is a perspective view of a cardiac pacing lead and the cardiac pacing lead package of the present invention prior to assembly.
Figure 7:
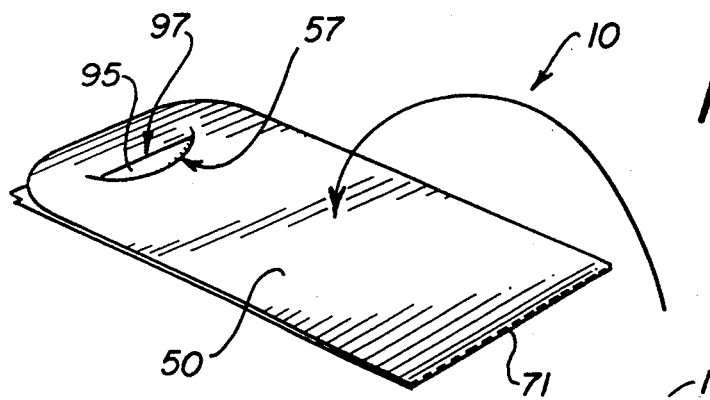

The cardiac pacing lead package 10 of the present invention is illustrated in FIGS. 1 and 2. The package 10 is seen to have a back cover panel 70. Back cover panel 70 is seen to have a substantially rectangular shape with a pair of opposed major sides and a pair of opposed minor sides. The first major side of panel 70 is seen to have an offset section such that the width of panel 70 in the offset section is less than the width of the panel adjacent to fold line 71. Foldably attached to back cover panel 70 along fold line 71 is the front cover panel 50. Front cover panel 50 is seen to be substantially rectangularly shaped having a pair of opposed minor sides and a pair of opposed major sides and is further seen to have, adjacent to its unattached minor side, slit 55 forming tab 56 and tab pocket 57. Extending from the offset portion of the first major side of back retention panel 70 is the tab member 80. Tab member 80 is foldably connected to the first major side of back retention panel 70 along fold line 81 in the offset section. Foldably mounted to the other major side of the back cover panel 70 along the fold line 91 is the front retention panel 90. The back cover panel 70 is seen to have slit 72 adjacent to front retention panel 90 forming tab 74 and tab pocket 73. Part of slit 72 is coextensive with fold line 91.

The front retention panel 90 is seen to be substantially rectangularly shaped with a pair of opposed major sides and a pair of opposed minor sides. Adjacent to a first minor side of the front retention panel 90 (adjacent to fold line 99) is the tab 95 and tab pocket 97 formed by slit 96. Foldably connected to the first minor side of the front retention panel 90 along fold line 99 is the base panel 20.

Base panel 20 is seen to be a substantially rectangularly shaped panel having a pair of opposed major sides and a pair of opposed minor sides. Base panel 20 is seen to be foldably connected along fold line 99 to a minor side of panel 90. Base panel 20 is seen to have cut outs 25 for receiving electrode needles. Base panel 20 is also seen to have a pair of needle park tabs 26 and tab pockets 28 formed by slits 27. Cut outs 25 and pockets 28 may be replaced by other conventional needle parks, including foam members, if desired.

Extending from the first minor side of base panel 20 are the winding tabs 40 having semicircular end sections 41. The tabs 40 are preferably spaced an equal distance from the longitudinal centerline of base panel 20. Extending from a first major side of the base panel 20 is the tab panel 45. The tab panel 45, which is foldably connected to the base panel 20 along fold line 46, is seen to have an irregular shape having rounded corner 47 and sloping portion 48.

Back retention panel 100 is seen to be substantially rectangularly shaped having a pair of opposed minor sides and opposed major sides. The back retention panel 100 is seen to be foldably connected along a first major side to the front retention panel 90 along fold line 101. Panel 100 is seen to have rounded corners 103 and angulated section 102. Back retention panel 100 is seen to have slit 105 adjacent to the first major side forming tab 106 and tab pocket 107. The back retention panel 100 is further seen to have slit 110 and fold line 111 forming tab panel 115. Slit 110 is perpendicular to, and extends through, the second major side of panel 100. The second major side of panel 100 is seen to be longer than the first major side. Adjacent to slit 110 and extending from the second major side of panel 100 is the tab member 109.

A temporary pacing wire 250 used for cardiac pacing is illustrated in FIG. 2. The pacing wire 20 is seen to have proximal needle electrode 235, having score line 236, and distal surgical needle 220. The pacing wire 200 is seen to have wire 201 having insulated section 210 and distal bare conductive section 215. Wire 201 is seen to have proximal end 202 and distal end 204. Needle electrode 230 is seen to be mounted to the proximal end 202 of wire 201. Surgical needle 220 is seen to be mounted to the distal end 204 of wire 201.

The assembly of a package 10 of the present invention is illustrated in FIGS. 3–8. To assemble the package 10 of the present invention, initially the electrode needles 230 are inserted through openings 25 in base panel 20. Then the base panel 20 is rotated clockwise about fold line 99 such that the base panel 20 is substantially parallel to, and resting upon, the front retention panel 90. The directions of rotation for the purposes of this description are referenced to an observer having a point of view as indicated by arrow 300. Then, the wire 201 of a first pacing wire 200 is wound about a tab member 40 and laid upon the base panel 20, preferably in a "figure 8" configuration. Next, the surgical needle 220 is placed into the tab pocket 28. The tab pockets 28, as previously mentioned serve as needle parks for the surgical needles 20. Then, the tab member 45 is rotated clockwise about fold line 46 so that it is resting upon the base panel 20. Next, the back retention panel 100 is rotated clockwise about the fold line 101 such that the back retention panel 100 is parallel to and rests upon the base panel 20 and section 210 of lead 200 and the panel 115 is rotated counterclockwise about fold line 11. Next, the second pacing wire 200 is mounted in a similar manner to the first pacing wire. Wire 201 is wound about a tab member 40 onto panels 100 and 20, and tab panel 115 is then rotated in a clockwise direction to secure wire 201. Next, the panels 20, 90 and 100 are rotated clockwise toward back cover panel 70 about the fold line 91 as the tab 80 is inserted into tab pocket 107 while tab 109 is inserted into tab pocket 73. Finally, the front cover panel 50 is folded counter clockwise about fold line 71 such that it is resting upon and parallel to front retention panel 90. Then tab 56 is inserted into tab pocket 97, thereby locking the package.

Figure 9:
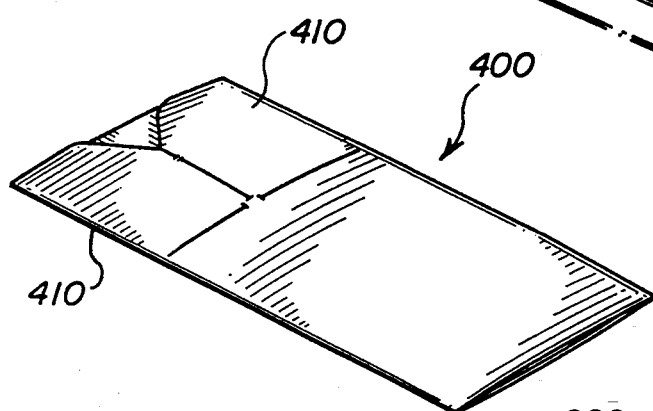
FIG. 9 is a perspective view of a cardiac pacing lead package of the prior art.
Figure 10:
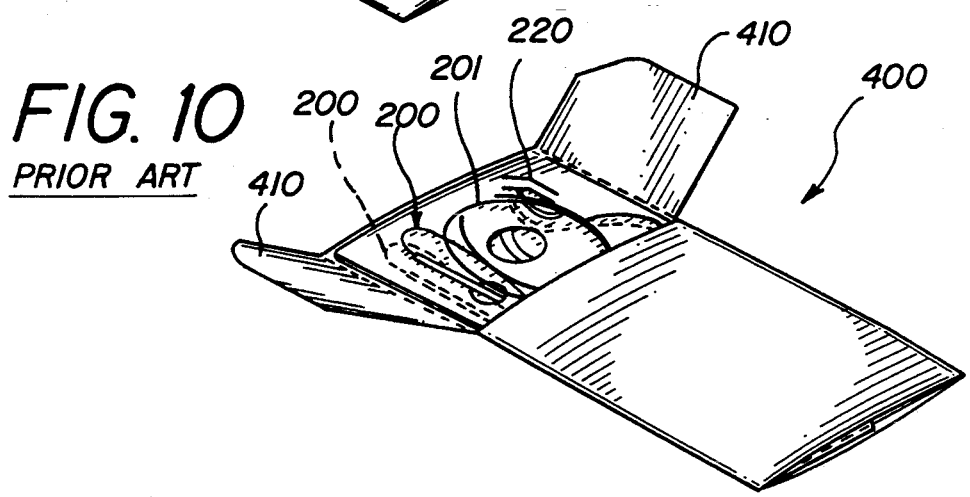
FIG. 10 is a perspective view of the prior art cardiac pacing lead package of FIG. 9 illustrating the location of the needles and leads within the package.

A package 400 of prior art is seen in FIGS. 9 and 10. The package 400 is seen to have front opening panels 410. Pacing wires 200 are seen to be stacked one on top of the other in the package. The package 400 of the prior art is seen to have several disadvantages. The needle 220 and wire 201 are in the same compartment. The wire 201 can interfere with the arming of the needle 220. Additionally, the needle/wire compartments are stacked one on top of the other. Accordingly, one needle/wire set must be removed before the other can be accessed. When two different color wires are used, the preferred color may be under the other needle/wire set.

The package 10 of the present invention has the following advantages. The needle/wire sets are next to each other for quick and easy delivery. Also, the needles and wires are separated in two different compartments.

The packages of the present invention may be constructed out of any material which is easily die cut and scored, and easily foldable, and which has sufficient strength and integrity to adequately protect the loop and catheter during sterilization, shipping, handling and storage. Such materials include conventional materials such as medical grade paperboard. It is particularly preferred to use a conventional, stiff paperboard having a thickness of about 0.008" to about 0.016". The paperboard, as previously mentioned, is preferably an appropriate medical grade. Other materials, including plastics, foils, and laminates combined with each other or with paper may also be used. The packages 10 are made using conventional equipment such as die cutting presses.

It will be appreciated by those skilled in the art that the size of the package 10 and the panels will vary in accordance with the size of the temporary pacing lead 200 and associated needles. The package 10 and the panels will be of sufficient size to effectively contain a particular temporary pacing lead 200 as illustrated and described herein.

Figure 8:
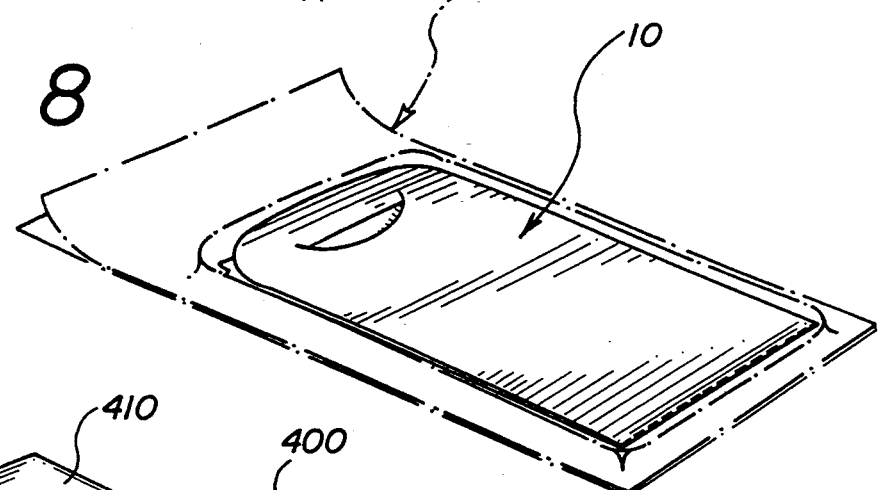
FIG. 8 is a perspective view of the assembled package of FIGS. 1-7 contained in an outer envelope; the outer envelope is shown in phantom.

The package 10 of the present invention containing the suture loop and cannula assembly 100 is typically further packaged by insertion into a conventional plastic envelope 180 or a conventional foil packet which is then sealed (see FIG. 8). Such a plastic envelope typically is made from conventional materials such as TYVEK ®, paper polyfoil, polyester copolymer, polypropylene copolymer, combinations thereof, and the like.

The packaged medical devices are typically sterilized using conventional sterilization equipment and processes. Examples of the sterilization processes which can be used on the temporary pacing wires 200 packaged in the foldable packages 10 of the present invention include conventional sterilization processes such as Co 60, irradiation, ethylene oxide, methylene bromide, and the like.

Although this invention has been shown and described with respect to the detailed embodiments thereof, it will be understood by those skilled in the art that various changes and further detail thereof may be made without departing from the spirit and scope of the claimed invention.

What is claimed:

1. A foldable package for a cardiac pacing wire, comprising:
   a base panel having a pair of substantially opposed major sides and substantially opposed minor sides;
   at least one winding tab extending from a first minor side of the base panel;
   means for receiving a surgical needle mounted to the base panel;
   means for receiving an electrode needle mounted to the base panel;
   a tab panel foldably connected to one major side of the base panel;
   a front retention panel foldably connected to the second minor side of the base panel, the front retention panel having a pair of substantially opposed major sides and a pair of substantially opposed minor sides;
   a tab pocket in the front retention panel for receiving a tab;
   a back cover panel having a pair of substantially opposed major sides and substantially opposed sides foldably connected along a first major side to a first major side of the front retention panel;
   a tab foldably connected to the second major side of the back cover panel;
   a tab pocket in back cover panel for receiving a tab;
   a front cover panel having a pair of substantially opposed major sides and a pair of substantially opposed minor sides foldably connected to a first minor side of the back cover panel;
   a tab pocket in the front cover panel;
   a back retention panel having a pair of opposed major sides and a pair of opposed minor sides foldably connected along a first major side to the second major side of front retention panel;
   a tab member extending from the second major side of back retention panel;
   a tab pocket in the back retention panel; and,
   a fold line and a slit in the back retention panel forming a tab member.

2. The package of claim 1 wherein the means for receiving the electrode needle comprises at least two holes in the base panel.

3. The package of claim 1 wherein the means for receiving a surgical needle comprises at least one tab and tab pocket in the base panel.

4. The combination comprising the package of claim 1 and a temporary cardiac pacing lead, wherein the cardiac pacing lead comprises a conductive wire having a distal end and a proximal end, a surgical needle mounted to the distal end, and an electrode needle mounted to the proximal end, wherein the wire is insulated and wherein a distal section of the wire adjacent to the distal end is uninsulated.

5. The package of claim 1 further comprising a sterile outer envelope.

* * * * *